United States Patent [19]
Vincenzo et al.

[11] Patent Number: 5,840,914
[45] Date of Patent: Nov. 24, 1998

[54] 3-(2-TRIALKYLSILYLOXY) ETHYL-7-1H-INDOLES AND METHOD FOR THEIR PREPARATION

[75] Inventors: Giobbio Vincenzo, Turin; Polastri Franco, Cusano Milanino-Mi, both of Italy

[73] Assignee: Teva Pharmaceutical Industries, Ltd., Petah Tiqva, Israel

[21] Appl. No.: 736,472

[22] Filed: Oct. 24, 1996

Related U.S. Application Data

[62] Division of Ser. No. 453,740, May 30, 1995, Pat. No. 5,599,946.

[51] Int. Cl.[6] .......................................................... C07F 7/18
[52] U.S. Cl. ............................................................. 548/406
[58] Field of Search ............................................... 548/406

[56] References Cited

U.S. PATENT DOCUMENTS 3,939,178  2/1976  Demerson et al. .
4,585,877  4/1986  Demerson et al. .

OTHER PUBLICATIONS

P. Ribéreau–Gayon et al., "Rural Economy.—Simultaneous analysis of organic acids, polyalchohols, and sugars in wine. Applications.", *C.R. Acad. Sc. Paris,* t. 273, Series D–1761, 8 Nov. 1971, 2 pages (together with English translation).

*Primary Examiner*—Patricia L. Morris
*Attorney, Agent, or Firm*—Kenyon & Kenyon

[57] ABSTRACT

The present invention relates to novel trialkylsilyloxy derivatives of 7-ethyltryptophol useful in the preparation of etodolac, and methods of making them, and methods of using them to prepare etodolac.

9 Claims, No Drawings

3-(2-TRIALKYLSILYLOXY) ETHYL-7-1H-INDOLES AND METHOD FOR THEIR PREPARATION

This application is a division of application Ser. No. 08/453,740, filed on May 30, 1995, now U.S. Pat. No. 5,599,946.

FIELD OF THE INVENTION

The present invention relates to novel trialkylsilyloxy derivatives of 7-ethyltryptophol, i.e., 3-(2-trialkylsilyloxy) ethyl-7-ethyl-1H-indoles, useful in the preparation of etodolac, methods of preparing them, and methods of using them to prepare etodolac.

BACKGROUND OF THE INVENTION

U.S. Pat. No. 3,939,178 discloses a genus of pyrano [3,4-b] indoles and a method of making them, which include the anti-inflammatory compound 1,8-diethyl-1,3,4,9-tetrahydropyrano[3,4-b]indole-1-acetic acid, also known as etodolac. The method which is generically disclosed, involves reacting 7-ethyltryptophol with methyl 3-oxopentanoate to generate etodolac methyl ester:

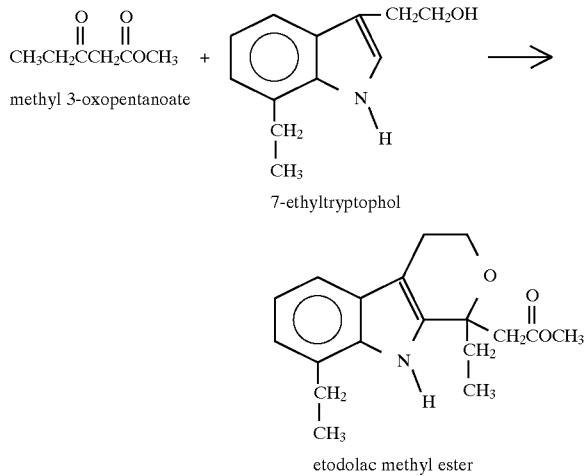

The etodolac methyl ester may then be converted to etodolac by basic hydrolysis of the ester group, as illustrated at column 1, lines 45–48 and at column 3, lines 39–41 of U.S. Pat. No. 4,585,877:

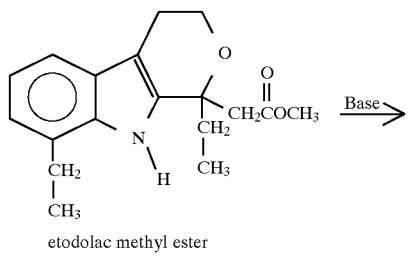

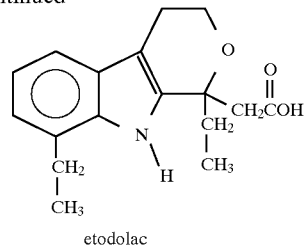

The synthesis of etodolac described in these patents requires flash chromatographic purification of 7-ethyltryptophol in order to produce etodolac of a pharmaceutical quality (see U.S. Pat. No. 4,585,877, Example 3). However, the use of flash chromatography in industrial scale bulk synthetic reactions is very expensive, time consuming, and cannot be performed on an industrial scale, and is for this reason disfavored.

SUMMARY OF THE INVENTION

It is therefore an object of the present invention to provide novel compounds useful for the efficient and cost-effective preparation of pharmaceutically acceptable etodolac on an industrial scale. In particular, it is an object of the invention to provide a method for making etodolac that does not require flash chromatography.

Accordingly, the invention provides a novel class of 3-(2-trialkylsilyloxy)ethyl-7-ethyl-1H-indole compounds useful for synthesizing etodolac. A preferred embodiment is 3-(2-trimethylsilyloxy)ethyl-7-ethyl-1H-indole.

The invention also provides methods for preparing these novel compounds, and methods for using these novel compounds for making etodolac without the need for flash chromatography.

In a preferred embodiment, an etodolac precursor, 7-ethyltryptophol, is reacted with a trialkylsilyl compound to produce a trialkylsyliloxy derivative of 7-ethyltryptophol which is subsequently converted to etodolac. In a more preferred embodiment, 7-ethyltryptophol is reacted with hexamethyldisilazane to yield 3-(2-trimethylsilyloxy)ethyl-7-ethyl-1H-indole. The 3-(2-trialkylsilyloxy)ethyl-7-ethyl-1H-indole is reacted with lower alkyl ketoester to form etodolac methyl ester, which is then converted into etodolac by acid or base hydrolysis.

DETAILED DESCRIPTION OF THE INVENTION

The present invention comprises novel 3-(2-trialkylsilyloxy)ethyl-7-ethyl-1H-indole compounds useful for making etodolac on an industrial scale, having the following formula I:

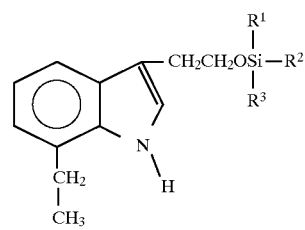

3-(2-trialkylsilyloxy)ethyl-7-ethyl-1H-indole wherein each of $R^1$, $R^2$ and $R^3$ are the same or different and each is an alkyl group of from 1–6 carbons. Thus, each alkyl group can be, for example, methyl, ethyl, propyl, isopropyl, butyl, isobutyl, tert-butyl, pentyl, isopentyl, or hexyl. Each alkyl preferably is methyl.

Examples of such trialkylsilyloxy derivatives include 3-(2-trimethylsilyloxy)ethyl-7-ethyl-1H-indole, 3-(2-triethylsilyloxy)ethyl-7-ethyl-1H-indole, 3-(2-tripropylsilyloxy)ethyl-7-ethyl-1H-indole, 3-(2-ethyldimethylsilyloxy)ethyl-7-ethyl-1H-indole, 3-(2-methyldiethylsilyloxy)ethyl-7-ethyl-1H-indole, 3-(2-tributylsilyloxy)ethyl-7-ethyl-1H-indole, and 3-(2-trihexyl)ethyl-7-ethyl-1H-indole. 3-(2-Trimethylsilyloxy)ethyl-7-ethyl-1H-indole is preferred.

The compounds of the invention are prepared by reacting 7-ethyltryptophol with a suitable trialkylsilyl compound of formula II:

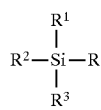

wherein R is:

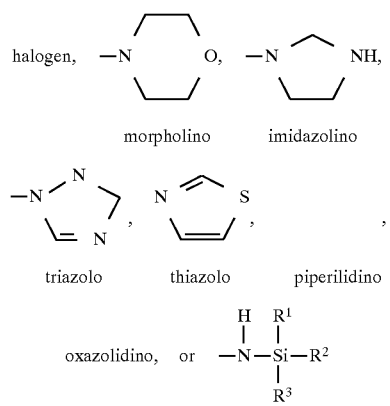

and $R^1$, $R^2$ and $R^3$ are as defined above, to yield the 3-(2-trialkylsilyloxy)ethyl-7-ethyl-1H-indole of Formula I.

Preferred trialkylsyliloxy compounds are the hexalkyldisilazanes, wherein each alkyl has from 1 to 6 carbons, with hexamethyldisilazane having the following formula being most preferred:

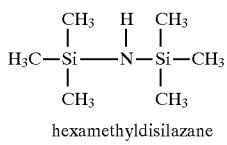

hexamethyldisilazane

The reaction is preferably performed in a non-polar solvent such as xylene or toluene at a temperature of 70°–72° C., for 1–2 hours. Preferably, the molar ratios of the trialkylsyliloxy reagent and the 7-ethyltryptophol are 1:3. The reaction is suitably carried out under reflux conditions. The reaction product is recovered by evaporation of the solvent, preferably under vacuum. The product is then isolated by distillation at high vacuum, preferably 0.5–2.0 mm Hg, at elevated temperatures, preferably 165°–185° C., to remove unreacted starting material.

When the trialkylsilyl compound used is a trimethylsilyl compound, such as hexamethyldisilazane, the product produced is 3-(2-trimethylsilyloxy)ethyl-7-ethyl-1H-indole having the formula:

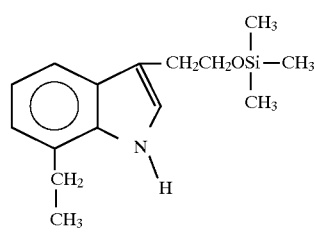

The trialkyl derivative of 7-ethyltryptophol of Formula I is converted to etodolac methyl ester by reacting it with a lower alkyl ketoester, preferably a lower alkyl ketoester of 3-oxo pentanoate, for example with methyl 3-oxopentanoate, under conditions described in U.S. Pat. No. 3,939,178:

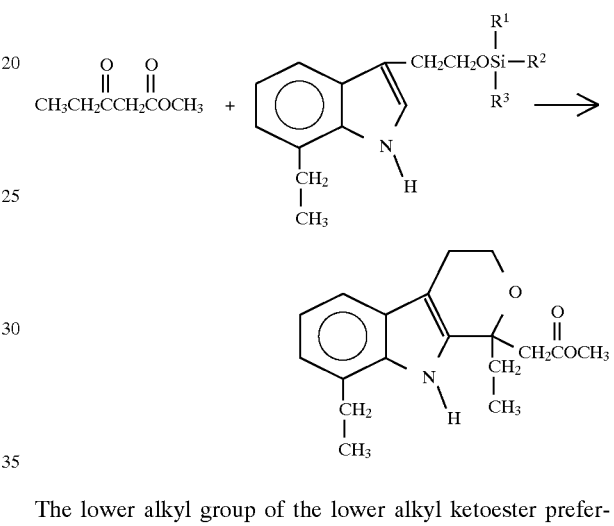

The lower alkyl group of the lower alkyl ketoester preferably is one having from 1 to 6 carbon atoms. Etodolac methyl ester may then be converted to etodolac via acid or base hydrolysis.

In contrast with the prior art methods, the present invention yields pharmaceutically acceptable etodolac without the need for cumbersome flash chromatographic purification. The methods taught herein yield pharmaceutically acceptable etodolac by routine extraction and distillation steps that are readily adapted for industrial scale production.

The following examples are intended to illustrate but not limit the invention.

EXAMPLE 1

Synthesis of 3-(2-Trimethylsilyloxy)Ethyl-7-Ethyl-1H-Indole Using Hexamethyldisilazane Hexamethyldisilazane (20.8 g, 0.1 mole) was added dropwise into a solution of 7-ethyltryptophol (17 g, 0.09 mole) and xylene (24 ml). The mixture was refluxed for two hours and then the xylene was evaporated. The product was distilled at a vacuum of 0.5 mm Hg, at a temperature of 175° to 185° C. The yield was 11.6 g (48%).

$^1$H-NMR(CDCl$_3$, 300 MHz): delta H; 0.1 (9H,s), 1.35 (3H,s), 2.84 (2H,q,J=8), 3.01 (2H,t,J=8), 3.84 (2H,t,J=8), 7.06 (3H,m), 7.46 (1H,d,j=8), 7.94 (1H,br s).

In a similar manner, other trialkylsilyl compounds may be used in place of hexamethyldisilazane to yield 3-(2-trialkylsilyloxy)ethyl-7-ethyl-1H-indole. For example, if hexaethyldisilazane is used instead of hexamethyldisilazane, the product is 3-(2-triethylsilyloxy)ethyl-7-ethyl-1H-indole;

if hexapropyldisilazane is used, the product is 3-(2-tripropylsilyoxy)ethyl-7-1H-indole; and if hexahexyldisilazane is used, the product is 3-(2-trihexylsilyoxy)-ethyl-7-ethyl-1H-indole.

EXAMPLE 2

Synthesis of 3-(2-Trimethylsilyloxy)Ethyl-7-Ethyl-1H-Indole Using 1-(Trimethlsilyl)Imidazole Following the procedures described in Example 1, 1-(trimethylsilyl)imidazole is reacted with 7-ethyl tryptophol in xylene to yield 3-(2-trimethylsilyloxy)ethyl-7-ethyl-1H-indole.

EXAMPLE 3

Synthesis of 3-(2-Trimethylsilyloxy)Ethyl-7-Ethyl-1H-Indole Using Chlorodimethylethylsilane Following the procedures described in Example 1, chlorodimethylethylsilane is reacted with 7-ethyl tryptophol in xylene to yield 3-(2-dimethylethylsilyloxy)ethyl-7-ethyl-1H-indole.

EXAMPLE 4

Synthesis of 3-(2-Trimethylsilyloxy)Ethyl-7-Ethyl-1H-Indole Using 1-(Trimethylsily)Imidazole Following the procedures described in Example 1, 1-(trimethylsilyl)imidazole is reacted with 7-ethyl tryptophol in xylene to yield 3-(2-trimethylsilyloxy)ethyl-7-ethyl-1H-indole.

EXAMPLE 5

Synthesis of 3-(2-Trimethylsilyloxy)Ethyl-7-Ethyl-1H-Indole Using 1-(Trimethylsilyl)Morpholine Following the procedures described in Example 1, 1-(trimethylsilyl)morpholine is reacted with 7-ethyl tryptophol in xylene to yield 3-(2-trimethylsilyloxy)ethyl-7-ethyl-1H-indole.

EXAMPLE 6

Synthesis of 3-(2-Trimethylsilyloxy)Ethyl-7-Ethyl-1H-Indole Using 1-(Trimethylsylil)Triazole Following the procedures described in Example 1, 1-(trimethylsilyl)triazole is reacted with 7-ethyl tryptophol in xylene to yield 3-(2-trimethylsilyloxy)ethyl-7-ethyl-1H-indole.

EXAMPLE 7

Synthesis of 3-(2-Trimethylsilyloxy)Ethyl-7-Ethyl-1H-Indole Using 1-(Trimethylsilyl)Thiazole Following the procedures described in Example 1, 1-(trimethylsilyl)thiazole is reacted with 7-ethyl tryptophol in xylene to yield 3-(2-trimethylsilyloxy)ethyl-7-ethyl-1H-indole.

EXAMPLE 8

Synthesis of 3-(2-Trimethylsilyloxy)Ethyl-7-Ethyl-1H-Indole Using 1-(Trimethylsilyl)Piperilidine Following the procedures described in Example 1, 1-(trimethylsilyl)piperilidine is reacted with 7-ethyl tryptophol in xylene to yield 3-(2-trimethylsilyloxy)ethyl-7-ethyl-1H-indole.

EXAMPLE 9

Synthesis of 3-(2-Trimethylsilyloxy)Ethyl-7-Ethyl-1H-Indole Using 1-(Trimethylsilyl)Oxazolidine Following the procedures described in Example 1, 1-(trimethylsilyl)oxazolidine is reacted with 7-ethyl tryptophol in xylene to yield 3-(2-trimethylsilyloxy)ethyl-7-ethyl-1H-indole.

EXAMPLE 10

Synthesis of 3-(2-Trihexylsilyloxy)Ethyl-7-Ethyl-1H-Indole Using Hexahexyldisilazane Following the procedures described in Example 1, hexahexyldisilazane is reacted with 7-ethyl tryptophol in xylene to yield 3-(2-trihexylsilyloxy)ethyl-7-ethyl-1H-indole.

EXAMPLE 11

Synthesis of Methyl 1,8-Diethyl-1,3,4,9-Tetrahydropyrano[3,4-b]Indole-1-Acetate (Etodolac Methyl Ester)

3-(2-trimethylsilyloxy)ethyl-7-ethyl-1H-indole (10 g, 0.038 mole) as synthesized in Example I was added to a mixture of methanol (60 ml) and water (6 ml) and refluxed in the presence of p-toluenesulfonic acid (0.26 ml). The solvent was evaporated and toluene (32 ml) was added to the remaining oily solution. Residual water was removed by azeotropic distillation, leaving a residue containing 3-(2-trimethylsilyloxy)ethyl-7-ethyl-1H-indole.

Methyl 3-oxopentanoate (5.6 g, 0.043 mole) (Aldrich) was added to a solution of the above-mentioned residue containing 3-(2-trimethylsilyloxy)ethyl-7-ethyl-1H-indole, toluene (70 ml) and methylene chloride (10 ml). Borontrifluoroetherate (2.58 g, 0.02 mole) was added dropwise into the reaction mixture under nitrogen. The contents were stirred for an hour, filtered from cellite, extracted with water (13 ml), sodium bicarbonate 2% solution (13 ml) and water (13 ml) again. The organic phase was evaporated to dryness and triturated with cold methanol (23 ml). The title compound was filtered, recrystallized from methanol (100 ml) and filtered again. Yield, 7.6 g (66%).

$^1$H-NMR (CDCl$_3$, 300 MHz): delta H; 0.83 (3H,t,J=7.5), 1.3.6 (3H,t,J=8), 2.02 (1H,m), 2.16 (1H,m), 2.76 (2H,m), 2.88 (2H,m). 2.92 (1H,d,J=18), 3.70 (3H,s), 3.94 (1H,m), 4.04 (1H,m), 7.00 (1H,br d,J=8), 7.06 (1H,t,J=8), 7.36 (1H,br,d,J=8), 9.06 (1H,br s).

In a similar manner, the 3-(2-trialkylsilyloxy)ethyl-7-ethyl-1H-indole of Examples 2–10 may be reacted with methyl 3-oxopentanoate or with other ketoesters to yield the methyl ester of etodolac.

EXAMPLE 12

1,8-Diethyl-1,3,4,9-Tetrahydropyranol[3,4-b]Indole-1-Acetic Acid (Etodolac)

Etodolac methyl ester (10 g, 0.03 mole) was added into a solution of potassium hydroxide (9 g, 0.16 mole), water (72 ml) and isopropyl alcohol (10 ml). The heterogeneous mixture was refluxed for half an hour. The solution was then cooled and acidified with hydrochloric acid to pH 2.3, and filtered on a buchnar funnel. The yield was 8.58 g (90%).

$^1$H-NMR(CDCl$_3$, 300 MHz): delta H; 0.88 (3H,t,J=8), 1.31 (3H,t,J=8), 2.04 (1H,m), 2.80 (2II,q,J=8), 2.84 (2H,m), 3.05 (2H,d,J=2), 4.08 (2H,m), 7.00 (1H,br d,J=8), 7.08 (1H,t,J=8), 7.36 (1H,br d,J=8), 8.62 (1H,br s).

We claim:

1. A 3-(2-trialkylsilyloxy)ethyl-7-ethyl-1H-indole, having the following formula:

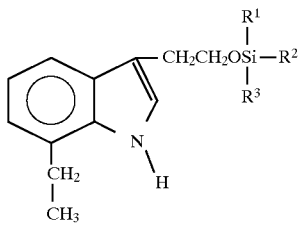

wherein $R^1$, $R^2$ and $R^3$ are the same or different, and each is an alkyl group having from 1 to 6 carbon atoms.

2. The 3-(2-trialkylsilyloxy)ethyl-7-ethyl-1H-indole compound according to claim 1, wherein said alkyl group is methyl, ethyl, propyl, isopropyl, butyl, iso-butyl, tert-butyl, pentyl, iso-pentyl, or hexyl.

3. The 3-(2-trialkylsilyloxy)ethyl-7-ethyl-1H-indole compound according to claim 2, wherein $R^1$, $R^2$ and $R^3$ are the same.

4. The 3-(2-trialkylsilyloxy)ethyl-7-ethyl-1H-indole compound according to claim 3, wherein $R^1$, $R^2$ and $R^3$ are methyl.

5. A method for preparing a 3-(2-trialkylsilyloxy)ethyl-7-ethyl-1H-indole of claim 1, comprising reacting 7-ethyltryptophol with a trialkylsilyl derivative having the formula II:

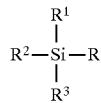

wherein R is:

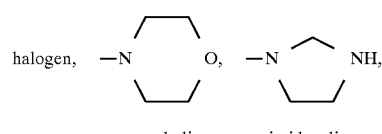

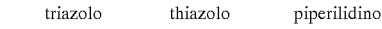

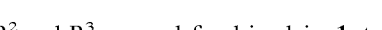

and $R^1$, $R^2$ and $R^3$ are as defined in claim 1, to yield said 3-(2-trialkylsilyloxy)ethyl-7-ethyl-1H-indole compound.

6. The method according to claim 5, wherein the reaction takes place in a non-polar solvent.

7. The method according to claim 6, wherein the non-polar solvent is xylene or toluene.

8. The method according to claim 5, wherein $R^1$, $R^2$ and $R^3$ are methyl.

9. The method according to claim 5, wherein said trialkylsilyl derivative is hexamethyldisilazane.

* * * * *